United States Patent [19]

Kim

[11] Patent Number: 5,576,017
[45] Date of Patent: *Nov. 19, 1996

[54] HETEROVESICULAR LIPOSOMES

[75] Inventor: Sinil Kim, Solana Beach, Calif.

[73] Assignee: DepoTech Corporation, San Diego, Calif.

[ * ] Notice: The term of this patent shall not extend beyond the expiration date of Pat. No. 5,422,120.

[21] Appl. No.: 393,724

[22] Filed: Feb. 23, 1995

Related U.S. Application Data

[63] Continuation-in-part of Ser. No. 78,701, Jun. 16, 1993, Pat. No. 5,422,120, which is a continuation-in-part of Ser. No. 496,846, Mar. 21, 1990, abandoned, which is a continuation-in-part of Ser. No. 196,590, May 30, 1988, abandoned.

[51] Int. Cl.$^6$ .................................................. A61K 9/127
[52] U.S. Cl. .............................. 424/450; 264/4.1; 264/4.3; 436/829
[58] Field of Search ........................... 424/450; 436/829; 264/4.1, 4.3

[56] References Cited

U.S. PATENT DOCUMENTS

| | | | |
|---|---|---|---|
| 4,883,665 | 10/1985 | Miyazima | 424/417 |
| 5,422,120 | 6/1995 | Kim | 424/450 |

OTHER PUBLICATIONS

Kim et al in Biochemica Biophysica Acta, vol. 728, pp. 339–348.

*Primary Examiner*—Gollamudi S. Kishore, PhD
*Attorney, Agent, or Firm*—Fish & Richardson P.C.

[57] ABSTRACT

Disclosed are heterovesicular liposomes containing substances of different biologically active compositions each encapsulated in separate chambers of the liposomes, having defined size distribution, adjustable average size, adjustable internal chamber size and number, methods of making them, and treatment of patients with them.

8 Claims, 3 Drawing Sheets

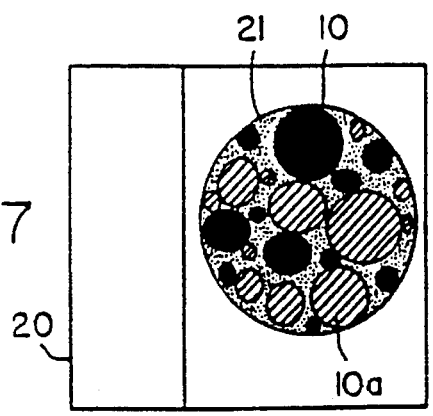
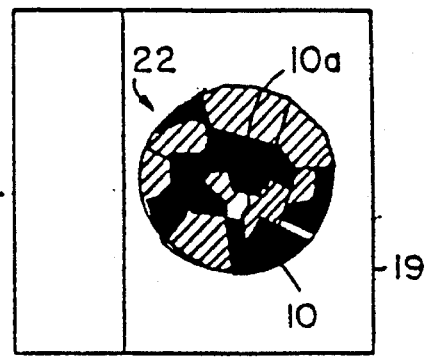
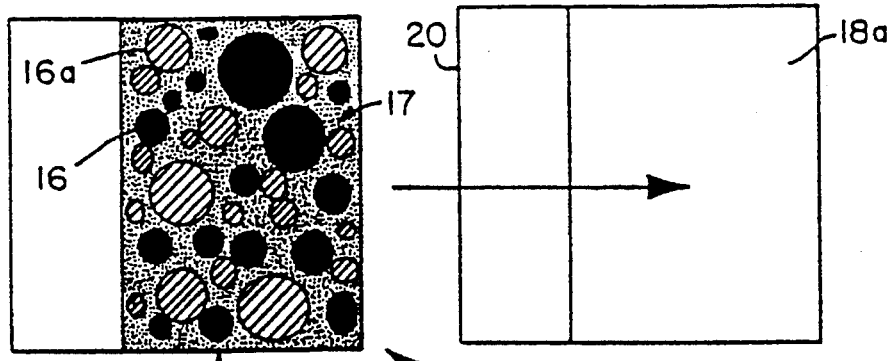
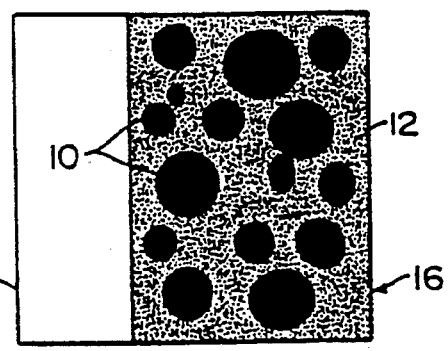
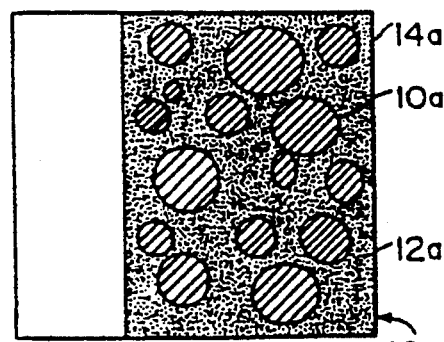
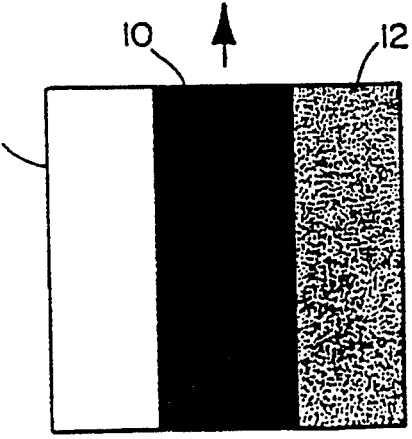
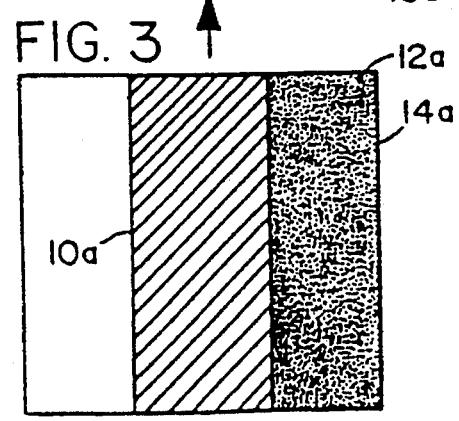

HETEROVESICULAR LIPOSOMES

CROSS-REFERENCE TO RELATED APPLICATIONS

The present invention is a continuation-in-part of application Ser. No. 08/078,701, filed Jun. 16, 1993, now U.S. Pat. No. 5,422,120 which is a continuation-in-part of Ser. No. 496,846, filed Mar. 21, 1990, now abandoned, which in turn is a continuation-in-part application of application Ser. No. 196,590, filed May 30, 1988, now abandoned.

BACKGROUND OF THE INVENTION

1. Field of the Invention

The invention relates to the synthetic heterovesicular lipid vesicles or liposomes, processes for their manufacture and encapsulation of various materials therein, and treatment of patients with them.

2. Description of Related Art

Multivesicular liposomes are one of the three main types of liposomes, first made by Kim, et al. (*Biochim. Biophys. Acta*, 782:339–348, 1983), and are uniquely different from the unilamellar (Huang, *Biochemistry*, 8:344–352, 1969; Kim, et al., *Biochim. Biophys. Acta*, 646:1–10, 1981) and multilamellar (Bangham, et al., *J. Mol, Bio.*, 13:238–252, 1965) liposomes in that there are multiple non-concentric aqueous chambers within. Previously described techniques for producing liposomes relate to the production of non-multivesicular liposomes; for example, U.S. Pat. Nos. 4,522, 803—Lenk, 4,310,506—Baldeschwieler, 4,235,871—Papahadjopoulos, 4,224,179—4,078,052—Papahadjopoulos, 4,394,372—Taylor, 4,308,166—Marchetti, 4,485,054—Mezei, and 4,508,703—Redziniak. For a comprehensive review of various methods of liposome preparation, refer to Szoka, et al. (*Ann. Rev. Biophys. Bioeng.*, 9:467–508, 1980).

Heterovesicular liposomes are lipid vesicles or liposomes characterized by multiple internal aqueous chambers. The lipid vesicles or liposomes with multiple internal aqueous chambers include, but are not limited to, multilamellar lipsomes, stable paucilamellar lipsomes and multivesicular lipsomes wherein the aqueous chambers are non-concentric. It is highly advantageous to provide a liposome delivery system in which two or more different substances are each encapsulated in separate compartments of a single liposome rather than encapsulated together in each compartment of the liposome.

SUMMARY OF THE INVENTION

The composition of the present invention comprises heterovesicular liposomes, i.e. lipid vesicles or liposomes with multiple internal aqueous chambers wherein a leuprolide-containing solution and a leuprolide-free solution are each encapsulated separately in different chambers within one liposome.

Briefly, the method of the invention comprises making a "water-in-lipid" emulsion by dissolving amphipathic lipids in one or more organic solvents for the first lipid component, adding an immiscible first aqueous component including leuprolide, preferably in the presence of phosphoric acid and sucrose, known herein as "the leuprolide containing solution," and then emulsifying the mixture mechanically. As used herein, the term "halogenohydroacid" means an acid represented by the formula HX, wherein X is a halogen (e.g., Br, F, Cl, I). The halogenohydroacids are typically obtained by dissolving the corresponding hydrogen halides (which can also be expressed as HX) in water. The preferred halogenohydroacid is hydrochloric acid (HCl).

In the emulsion, the water droplets suspended in the organic solvent will form the internal aqueous chambers, and the monolayer of amphipathic lipids lining the aqueous chambers will become one leaflet of the bilayer membrane in the final product. A second lipid component is then formed by dissolving amphipathic lipids in a volatile organic solvent and adding an immiscible second aqueous component including phosphoric acid and sucrose, and known herein as "the leuprolide-free solution." A second emulsion is then created. A chimeric emulsion is then formed by combining the first and second emulsions. The chimeric emulsion consists of multiple water droplets suspended in organic solvent wherein the leuprolide-containing solution and the leuprolide-free solution are each encapsulated separately in different aqueous droplets. The chimeric emulsion is then immersed in a third aqueous immiscible component preferably containing one or more nonionic osmotic agents and acid-neutralizing agent of low ionic strength and then mechanically dividing it to form solvent spherules suspended in the third aqueous component. The solvent spherules contain multiple aqueous droplets wherein the leuprolide-containing solution and the leuprolide-free solution are each encapsulated separately in different aqueous droplets within a single solvent spherule. The volatile organic solvent is evaporated from the spherules, preferably by passing a stream of gas over the suspension. When the solvent is completely evaporated, the spherules convert into heterovesicular liposomes with multiple internal aqueous chambers wherein leuprolide and phosphoric acid are encapsulated separately in different chambers within one liposome.

Accordingly, it is an object of the present invention to provide a heterovesicular lipid vesicle or liposome having a leuprolide-containing solution and a leuprolide-free solution, each encapsulated separately in different chambers of the vesicle or liposome.

A further object of the present invention is the provision of a heterovesicular liposome having a leuprolide-containing solution and a leuprolide-free solution, each encapsulated separately in chambers of the liposome in the presence of phosphoric acid which slows the leakage of them.

It is a further object of the present invention to provide a heterovesicular liposome having a leuprolide-containing solution and a leuprolide-free solution, each encapsulated separately in chambers of the liposome in the presence of phosphoric acid and a neutralizing agent.

It is a further object of the present invention to provide methods of producing such heterovesicular lipid vesicles or liposomes.

It is a further object of the present invention to provide processes for producing such heterovesicular lipid vesicles or liposomes by providing a first lipid component dissolved in one or more organic solvents and adding to the lipid component an immiscible first aqueous component containing a first substance to be encapsulated, forming a first water-in-oil emulsion from the first two immiscible components, providing a second lipid component dissolved in one or more organic solvents and adding into the lipid component an immiscible second aqueous component containing a second substance to be encapsulated, forming a second water-in-oil emulsion from the second two immiscible components, forming a chimeric emulsion by combining the first water-in-oil emulsion and second water-in-oil emulsion, transferring and immersing the chimeric emulsion into a third immiscible aqueous component, dispersing the chimeric emulsion to form solvent spherules containing multiple droplets of the first aqueous component containing the first substance and the second aqueous component containing the second substance, and evaporating the organic solvent from the solvent spherules to form the heterovesicular lipid vesicles or liposomes.

It is a further object of the present invention to provide a method for the treatment of a patient with at least two separate biologically active substances of different compositions by administering them to the patient encapsulated separately in chambers of a heterovesicular vesicle or liposome.

Other and further objects, features and advantages of the invention appear throughout the specification and claims.

BRIEF DESCRIPTION OF THE DRAWINGS

FIG. 1 is a schematic representation of a first aqueous substance added to a first lipid component in a vial.

FIG. 2 is a schematic representation of a first water-in-oil emulsion containing the aqueous substance and lipid components of FIG. 1.

FIG. 3 is a schematic representation of a two phase system in a vial containing a second aqueous component and a second lipid component.

FIG. 4 is a schematic representation of a water-in-oil emulsion formed from the aqueous component and lipid component of FIG. 3 by shaking.

FIG. 5 is a schematic representation of a chimeric emulsion made by mixing together the water-in-oil emulsion of FIG. 2 and the water-in-oil emulsion of FIG. 4.

FIG. 6 is a schematic representation of a vial containing an immiscible aqueous component into which the chimeric emulsion of FIG. 5 is introduced.

FIG. 7 is a schematic representation of solvent spherules containing droplets of the first and second aqueous components.

FIG. 8 is a schematic representation of the heterovesicular liposome formed by evaporation of solvent from the solvent spherules of FIG. 7.

DESCRIPTION OF THE PREFERRED EMBODIMENTS

Figure 9:
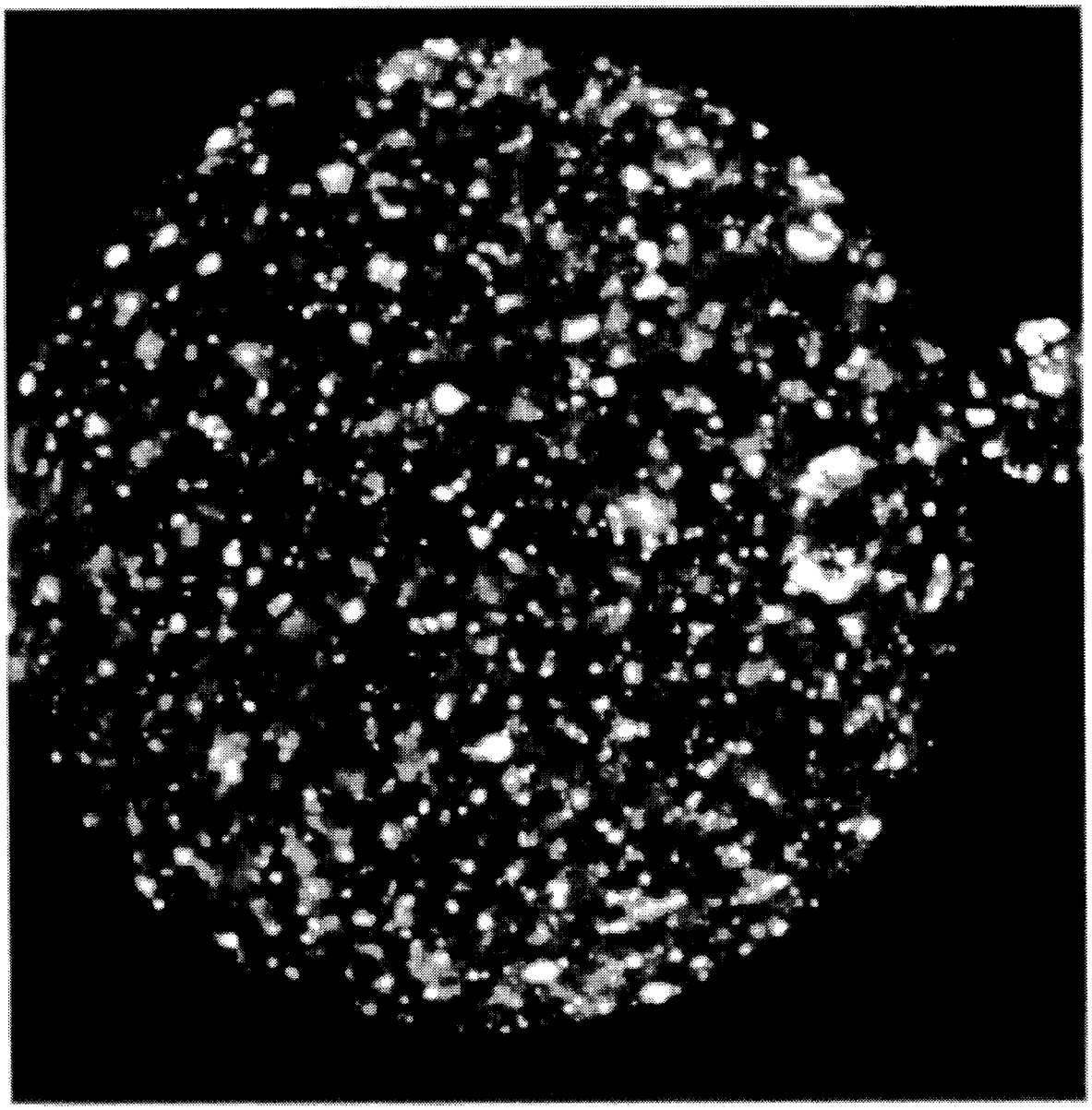
FIG. 9 is a confocal micrograph of a heterovesicular liposome showing two different sets of internal chambers, the first containing Texas-red-dextran, which is fluorescent, and the second containing no Texas-red dextran, which is dark. Magnification is 834×.

The term "multivesicular liposomes" as used throughout microscopic lipid vesicles consisting of lipid bilayer membranes, enclosing multiple the specification and claims means man-made, non-concentric aqueous chambers which all contain the same component. In contrast, the term "heterovesicular liposomes" as used throughout the specification and claims means man-made, microscopic liquid vesicles consisting of lipid bilayer membranes enclosing multiple, aqueous chambers wherein at least two of the chambers separately contain substances of different compositions. The microscopic lipid vesicles include but are not limited to multilamellar liposomes, stable paucilamellar multivesicular liposomes, wherein the vesicles are arranged non-concentrically.

The term "chimeric emulsion" as used throughout the specification and claims means an emulsion that consists of multiple water droplets suspended in organic solvent where the substances of two different compositions are each dissolved separately in different sets of aqueous droplets.

The term "solvent spherule" as used throughout the specification and claims means a microscopic spheroid droplet of organic solvent, within which is multiple smaller droplets of aqueous solution. The solvent spherules are suspended and totally immersed in a second aqueous solution.

The term "neutral lipid" means oil or fats that have no membrane-forming capability by themselves and lack a hydrophilic "head" group.

The term amphipathic lipids means those molecules that have a hydrophilic "head" group and hydrophobic "tail" group and have membrane-forming capability.

The composition of the present invention is a heterovesicular lipid vesicle or liposome having at least two substances of different compositions, each encapsulated separately in different chambers of the vesicle or liposome.

As used herein, the term "biologically active", when used to describe substances present in the chambers of the heterovesicular liposome, includes substances which possess biological activity in the form as presented in the vesicle as well as substances which become active after release from the vesicle chamber (i.e., possess "quiescent" biological activity). For example, in the latter instance, a first vesicle chamber could contain an enzyme and a second vesicle chamber could contain a prodrug which is convened upon interaction with the enzyme into an active moiety with therapeutic activity. Alternatively, the invention embraces a first vesicle chamber containing a substance possessing quiescent biological activity and a second vesicle chamber containing a substance possessing a different quiescent biological activity; where, upon release from their respective chambers, the substances interact with each other or components of the in vivo biological melieu such that both substances become biologically active in vivo. For example, a first vesicle chamber could contain the inactive compound 5-fluorocytosine (5-FC) and a second vesicle chamber could contain the enzyme cytosine deaminase. When cytosine deaminase is released from its vesicle and interacts with 5-FC released from its vesicle, the biologically active antitumor drug 5-fluorouracil (5-FU) is produced.

In addition, biologically active substances which can be incorporated include substances which act indirectly. For example, various excipients and stabilizers may be present. Such substances may act, for example, to increase the shelf life or bioavailability of a particular drug. Alternatively, many substances commonly classified as excipients may actually possess direct biological activity from very slight to quite significant. For example, the common excipient mannitol can also act biologically as a diuretic and even water may act biologically to affect dehydration. Such indirectly active substances include aqueous or non-aqueous solutions, suspensions, and emulsions. Examples of non-aqueous solutions are propylene glycol, polyethylene glycol, vegetable oils such as olive oil, and injectable organic esters such as ethyl oleate. Aqueous carriers include water, alcoholic-aqueous solutions, emulsions. or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like (see, *Remingtons Pharmaceutical Sciences*, 16th Ed., A. Oslo, ed., Mack, Easton, Pa. 1980). Those of ordinary skill in the art can readily ascertain and envision various combinations of compounds which can be utilized in the vesicles of the invention without resorting to undue experimentation.

A preferred method of making the heterovesicular vesicle or liposome is illustrated in the drawing to which reference is now made. As shown in FIG. 1, in step 1 a first aqueous substance of composition 10 to be encapsulated is added to a first lipid component 12 in the vial 14. The vial 14 is sealed mad in step 2 is mixed and shaken, such as being attached to the head of a vortex mixer to form the first water-in-oil emulsion 16 shown in FIG. 2 containing the first substance of composition 10 to be encapsulated. In a second vial 14a, a second aqueous substance 10a to be encapsulated is added to a second lipid component 12a, as shown in FIG. 3, and the vial 14a is sealed and in step 4 is mixed, such as being attached to the head of a vortex mixer to form a second water-in-oil emulsion 16a containing the substance of composition 10a to be encapsulated.

In step 5 the first 16 and second 16a water-in-oil emulsions are added together and mixed, such as by hand to make a "chimeric" emulsion, as shown in FIG. 5.

In step 6, as shown in FIG. 6, a portion of the chimeric emulsion from step 5 is individually added to vials 20 containing a third immiscible aqueous component 18a such as by squirting rapidly through a narrow tip pasteur pipette into two one-dram vials, here shown as one.

Figure 10:
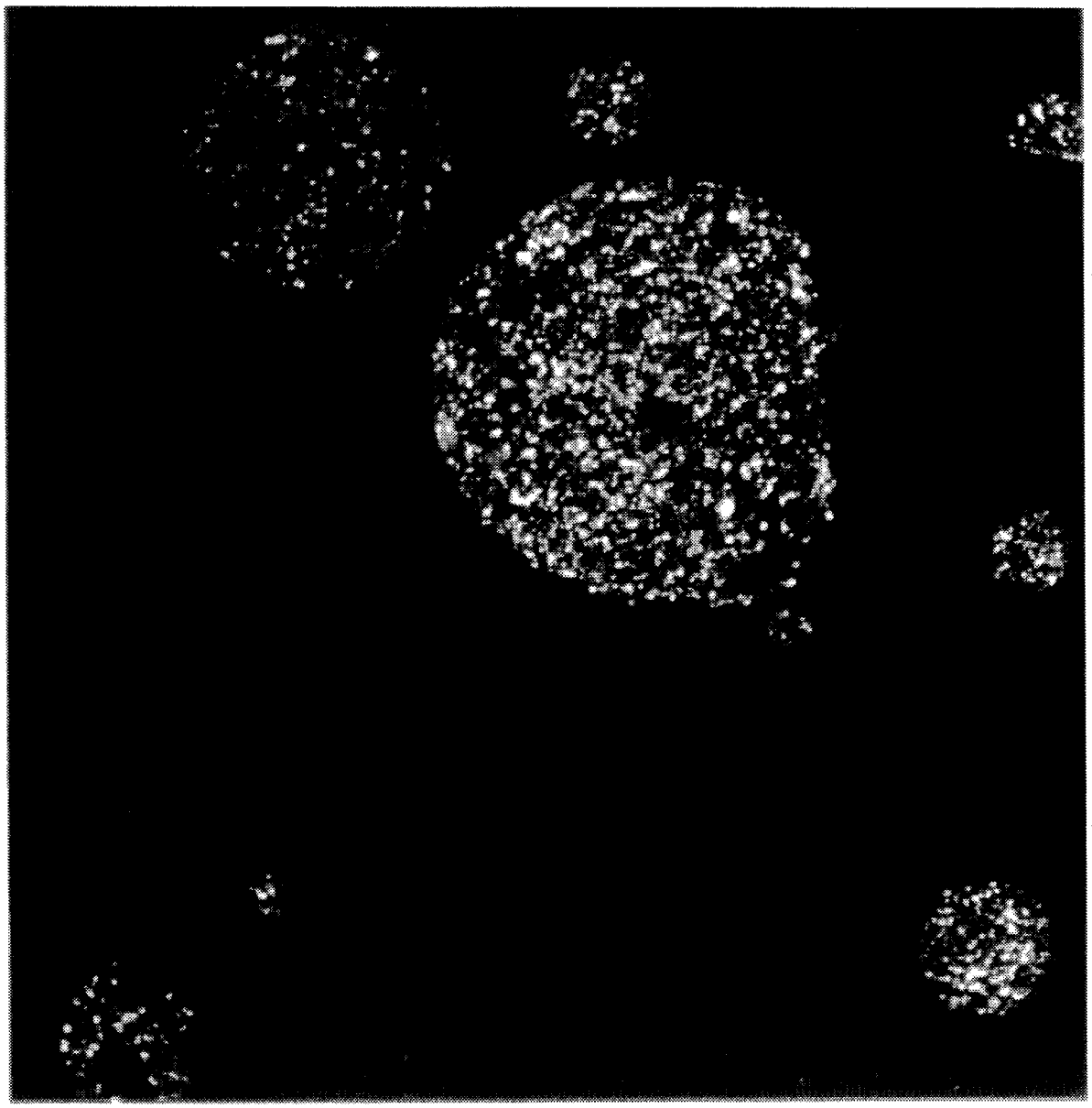
FIG. 10 is a scanning electron micrograph of heterovesicular liposomes showing two different sets of internal chambers, the first containing Texas-red-dextran, which is fluorescent, and the second containing no Texas-red dextran, which is dark. Magnification is 2645×.

In step 7 vials from step 6 are shaken, such as by a vortex mixer, and in step 8 the chloroform spherule suspension (as shown in FIG. 7) in each vial is transferred from step 7 and the chloroform is evaporated, such as by a stream of nitrogen gas, thereby providing the heterovesicular liposome 22 (as shown in FIG. 8) that contains a first substance in one or more internal aqueous chambers and a second substance in the remaining internal aqueous chambers within a single liposome. FIGS. 9 and 10 are confocal micrographs showing liposomes containing two sets of chambers, the first set of chambers encapsulating Texas-red-dextran dye, and the second set of chambers encapsulating no dye.

In alternative embodiments, each of the substances to be encapsulated is encapsulated in the presence of a halogenohydroacid, such as hydrochloric acid, which slows its leakage rate from the liposome or vesicle. The halogenohydroacid can be HCl, HI, or HBr. Other hydrochlorides which are satisfactory include, but are not limited to, guanine hydrochloride, glucosamine hydrochloride, lysine hydrochloride, histidine hydrochloride, arginine hydrochloride, and combinations thereof, which can be neutral, acidic, or basic.

Preferably, each of the substances to be encapsulated is encapsulated in the presence of phosphoric acid, which slows its leakage rate from the liposome or vesicle.

The heterovesicular liposomes may be administered by any desired route; for example, intrathecal, intraperitoneal, subcutaneous, intravenous, intralymphatic, oral, and submucosal, under many different kinds of epithelia including the bronchialar epithelia, the gastrointestinal epithelia, the urogenital epithelia, and various mucous membranes of the body, and intramuscular.

The heterovesicular liposomes may be modified in order to impart organ or cell target specificity. Such modifications may be particularly relevant for using the vesicles of the invention to administer drugs which are highly toxic or capable of inducing severe side effects, such as taxol or other anti-neoplastic agents which might otherwise not be utilized in view of their deleterious effects on normal tissues when systemically disseminated.

The targeting of liposome has been classified based on whether the targeting is passive or active. Passive targeting utilizes the natural tendency of the liposomes to distribute to cells of the reticulo-endothelial system (RES) in organs which contain sinusoidal capillaries without alteration of the surfaces of the liposome. Active targeting, on the other hand, requires alteration of the liposome surface by coupling the liposome to a specific ligand such as a monoclonal antibody, sugar, glycolipid, or protein that targets to a specific body site, or by changing the composition or size of the liposome in order to achieve targeting to organs and cell types other than the naturally occurring sites of localization (see, for example, *Remington's Pharmaceutical Sciences*, Gannaro, A. R., ed., Mack Publishing, 18 Edition, pp. 1691–1693, 1990, incorporated by reference).

To achieve active targeting the surface of the liposome may be modified in a variety of ways. For instance, lipid groups can be incorporated into the lipid bilayer of the liposome in order to maintain a targeting ligand in stable association with the liposomal bilayer. Alternatively, various linking groups can be used for joining the lipid chains of the liposome to a targeting ligand (Mannino, et al., *Bio Techniques*, 6(7):682, 1988, incorporated by reference). The compounds bound to the surface of the targeted delivery system may vary from small haptens of from about 125–200 molecular weight to much larger antigens with molecular weights of at least about 6 KD, but generally of less than $10^6$ KD. Proteinaceous ligand and receptors are of particular interest.

In the present invention, antibodies are preferred targeting ligands (U.S. Pat. Nos. 4,806,466 and 4,957,735; incorporated by reference). Antibodies can be used to target liposomes to specific cell-surface sites. For example, certain antigens expressed specifically on tumor cells, referred to as tumor-associated antigens (TAAs), may be exploited for the purpose of targeting anti-tumor antibody-containing liposomes directly to a malignant tumor. Since the composition incorporated in the liposome may be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or $F(ab')_2$, as long as they bind efficiently to the antigenic epitope on the target cells. Liposomes may also be targeted to cells expressing receptors for hormones or other serum factors (Malone, et al., *Proc. Nat'l. Acad. Sci*, USA, 86:6077, 1989; Gregoriadis, *Immunology Today*, 11(3):89, 1990; both incorporated by reference).

The heterovesicular liposomes can be administered to the patients in the normal manner when it is desirable to provide two separate biologically active compounds to the patient for the particular purpose of treatment desired.

The dose range appropriate for human use includes the range of 1–6000 mg/m to body surface area. The reason that this range is so large is that for some applications, such as subcutaneous administration, the dose required may be quite small, but for other applications, such as intraperitoneal administration, the dose desired to be used may be absolutely enormous. While doses outside the foregoing dose range may be given, this range encompasses the breadth of use for practically all the biologically active substances.

The multivesicular liposomes may be administered by any desired route; for example, intrathecal, intraperitoneal, subcutaneous, intravenous, intralymphatic, oral and submucosal, under many different kinds of epithelia including the bronchialar epithelia, the gastrointestinal epithelia, the urogenital epithelia, and various mucous membranes of the body, and intramuscular.

When encapsulating more than two substances separately in chambers of a liposome, a third (or fourth) aqueous component containing the third or fourth biologically active substance is formed, mixed to form a third or fourth water-in-oil emulsion, and then combined with the first and second emulsions and mixed to form a "chimeric" emulsion containing the three or more biologically active substances. The remainder of the process is the same as described when encapsulating two biologically active compounds or substances.

The present invention, therefore, obtains the objects and ends and has the advantages mentioned as well as others inherent therein.

The following examples set forth presently preferred methods of encapsulating two substances of different compositions in separate chambers of a vesicle or liposome.

EXAMPLE 1

Preparation of Dideoxycytidine/Glucose Heterovesicular Liposomes

Step 1: A first aqueous substance (one ml of 20 mg/ml dideoxycytidine solution in water with 0.1N hydrochloric acid) was added into a one-dram vial containing the first lipid component (9.3 µmoles of dioleoyl lecithin, 2.1 µmoles of dipalmitoyl phosphatidylglycerol, 15 µmoles of cholesterol, 1.8 µmoles of triolein and one ml of chloroform).

Step 2: The first vial was sealed and attached to the head of a vortex mixer and shaken at maximum speed for 6 minutes to form the first water-in-oil emulsion.

Step 3: In second vial, the second aqueous substance (one ml of 30 mg/ml glucose solution in water with 0.1N hydrochloric acid) was added into the second lipid component (which is identical to the first lipid component).

Step 4: The second vial was sealed and attached to the head of a vortex mixer and shaken at maximum speed for 6 minutes to form the second water-in-oil emulsion.

Step 5: 0.5 ml of the first emulsion was added to the second vial and mixed by hand to make a "chimeric" emulsion.

Step 6: Half of the "chimeric" emulsion was individually squirted rapidly through a narrow tip Pasteur pipette into one-dram vials, each containing a third immiscible aqueous component (2.5 ml water, 32 mg/ml glucose, 40 mM free-base lysine.

Step 7: The vials from step 6 were shaken on the vortex mixer for 3 seconds at "5" setting to form solvent spherules containing multiple droplets of the first and second aqueous substances within.

Step 8: The chloroform spherule suspensions in each vial was transferred into the bottom of a 2 L beaker containing 4.5 ml of water, 35 mg/ml glucose, and 22 mM free-base lysine. A stream of nitrogen gas at 7 L/rain was flushed through the beaker to evaporate chloroform over 5 minutes at 15° C.

The above example describes a method of making heterovesicular liposomes which separately contain glucose in approximately ⅚ of the internal aqueous chambers and separately contain dideoxycytidine in the remaining ⅙ of the internal aqueous chambers within a single liposome. Heterovesicular liposomes containing dideoxycytidine solution as one aqueous substance and glucose as the second aqueous substances were markedly more stable than non-heterovesicular liposomes.

EXAMPLE 2

This example is for the synthesis of heterovesicular liposomes containing IL-2 (interleukin-2) and lysine hydrochloride: For each batch of liposomes prepared, one ml of water containing 10 mg/ml HSA (Human serum albumin), 1 µg of IL-2, 200 mM lysine HCl pH 7.13 was added into a one-dram vial containing 9.3 µmoles of dioleoyl lecithin, 2.1 µmoles of dipalmitoyl phosphatidylglycerol, 15 µmoles of cholesterol, and 1.8 µmoles of triolein and one ml of chloroform (this is the first water-in-oil emulsion). For the second water-in-oil emulsion, 1 ml of lysine HCl (without IL-2) was added into one-dram vial containing 9.3 µmoles of dioleoyl lecithin, 2.1 µmoles of dipalmitoyl phosphatidylglycerol, 15 µmoles of cholesterol, and 1.87 µmoles of triolein, and one ml of chloroform. Each of the two vials was individually attached to the head of a vortex mixer and shaken sequentially at the maximum speed for 6 minutes.

0.5 ml of the first water-in-oil emulsion was added to the 2 ml of the second emulsion and mixed to make a "chimeric" water-in-oil emulsion. Half of the "chimeric" emulsion was individually squirted rapidly through a narrow tip Pasteur pipette into one-dram vials, each containing 2.5 ml of 4% glucose in water and 0.1 ml of lysine free base, 200 mM, and shaken at maximum speed for 3 seconds to form chloroform spherules. The chloroform spherule suspensions were transferred into a 250 ml Erlenmeyer flask containing 5 ml of 4% glucose in water and 0.2 ml of lysine free base, 200 mM. A stream of nitrogen gas at 7 L/min was flushed through the flask to evaporate chloroform over 5 minutes at 37° C.

EXAMPLE 3

This example is for the synthesis of heterovesicular liposomes containing ara-C solution as he first aqueous substance and distilled water as the second aqueous substance. For each batch of liposomes prepared, one ml of water containing 100 mg/ml ara-C, pH 1.1 was added into a one-dram vial containing 9.3 µmoles of dioleoyl lecithin, 2.1 µmoles of dipalmitoyl phosphatidylglycerol, 15 µmoles of cholesterol, and 1.8 µmoles of triolein, and one ml of chloroform, attached to the head of the vortex mixer and shaken at maximum speed for 6 minutes (this is the first water-in-oil emulsion). For the in situ generation of the second water-in-oil emulsion, ½ of the content was removed from the first water-in-oil emulsion, and then 1 ml of distilled water was added into the remaining first water-in-oil emulsion and the one-dram vial was shaken for 10 seconds at maximum speed. This resulted in a "chimeric" water-in-oil emulsion. Half of the "chimeric" emulsion was individually squirted rapidly through a narrow tip Pasteur pipette into one-dram vials, each containing 2.0 ml of 4% glucose in water and 0.5 ml of lysine free base, 200 mM, and shaken at maximum speed for 3 seconds to form chloroform spherules. The chloroform spherule suspensions were transferred into a 250 ml Edenmeyer flask containing 4 ml of 4% glucose in water and 0.5 ml of lysine free base, 200 mM. A stream of nitrogen gas at 7 L/min was flushed through the flask to evaporate chloroform over 5 minutes at 37° C.

EXAMPLE 4

Synthesis of Heterovesicular Liposomes Containing Granulocyte-Macrophase Colony Stimulating Factor (GM-CSF)

Exactly the same procedure was used as in Example 2 except IL-2 was replaced with 1 µg of GM-CSF.

EXAMPLE 5

Synthesis of Heterovesicular Liposomes of Various Lipid Composition, and Incorporation of Various Materials into Liposomes In place of using dioleoyl lecithin, dipalmtoyl phosphatidylglyerol, cholesterol, and triolein (TO), and other amphipathic lipids such as phosphatidyl cholines (PC), cardiolipin (CL), dimyristoyl phosphatidylglycerol (DMPG), phosphatidyl ethanolamines (PE), phosphatidyl serines (PS), dimyristoyl phosphatidic acid (DMPA), and other neutral lipids, such as tricaprylin (TC), in various combination can be used with similar results. For example, PC/C/CL/TO in 4.5/4.5/1/1 molar ration; DOPC/C/PS/TO in 4.5/4.5/1/1 molar ratio; PC/C/DPPG/TC in 5/4/1/1 molar ratio; PC/C/PG/TC in 5/4/1/1 molar ratio; PE/C/CL/TO in 4.5/4.5/1/1 molar ratio; and PC/C/DMPA/TO in 4.5/4.5/1/1 molar ratio can all be used. To incorporate other water-soluble materials, such as glucose, sucrose, methotrexate, or Ponceau S, simply substitute the desired materials for IL-2 in Example 2. Also, other biologically active substances in suitable doses can be similarly substituted for IL-2 as in Example 2.

EXAMPLE 6

In this example, the triolein in lipid components of above examples are substituted either singly or in combination by other triglycerides, vegetable oils, animal fats, tocopherols, tocopherol esters, cholesteryl esthers, or hydrocarbons with good results.

EXAMPLE 7

To make liposomes smaller than that in the foregoing examples, and with reference to Examples 1 or 2, the mechanical strength or duration of shaking or homogenization in Step 4 of Example 1 or 2 was increased. To make liposomes larger, the mechanical strength or duration of shaking or homogenization in Step 4 of Example 1 or 2 was decreased.

EXAMPLE 8

This example is for the synthesis of heterovesicular liposomes containing leuprolide and phosphoric acid. For each batch of liposomes prepared, two ml of water containing 80 mg/ml of leuprolide acetate, 0.2 mMoles of phosphoric acid, and 0.16 g of sucrose were added to a first 50 ml conical teflon tube containing 14.6 µmoles of triolein, 16.65 µmoles of dipalmitoyl phosphatidylglycerol, 78.88 µmoles of dioleoyl lecithin, 118.8 µmoles of cholesterol, and 2.0 ml of chloroform to be used in formation of the first water-in-oil emulsion. Six ml of water containing 0.75 mMoles of phosphoric acid and 0.42 g of sucrose were added to a second 50 ml conical teflon tube containing 43.8 µmoles of triolein, 49.95 µmoles of dipalmitoyl phosphatidylglycerol, 236.6 µmoles of dioleoyl lecithin, 356.49 µmoles of cholesterol, and 6.0 ml of chloroform to be used in preparation of the second water-in-oil emulsion. The two conical teflon tubes were sequentially attached to a TK homogenizer with the mixing blade level at the interface of the mixture, and the contents were homogenized at 10,000 rpm for 7 minutes to obtain the first and second water-in-oil emulsions.

A chimeric water-in-oil emulsion was formed by adding the first water-in-oil emulsion to the second water-in-oil emulsion and gently homogenizing the mixture at 2,000 rpm for 2 minutes. Then 25 ml of water containing 4 ml of 50% glucose and 0.29 g of lysine free base were added to the chimeric water-in-oil emulsion and mixing was continued at 4,000 rpm for 15 seconds with the mixing blade 1 cm above the interphase to form a suspension of chloroform spherules. The suspension of chloroform spherules was transferred into a 250 ml Erlenmeyer flask containing 25 ml of water containing 4 ml of 50% glucose in water and 0.29 g of lysine free base. Heterovesicular liposomes having a leuprolide-containing solution and a leuprolide-free solution encapsulated in separate compartments were obtained by flushing the flask for 15 minutes with a stream of nitrogen gas at rate of 7 L/rain and temperature of 37° C. to evaporate the chloroform.

While examples of the invention have been given for the purpose of disclosure, changes can be made therein which are within the spirit of the invention as defined by the appended claims.

I claim:

1. A heterovesicular liposome comprising at least two compounds in separate solutions encapsulated in separate chambers of the liposome; wherein one and only one of the compounds is leuprolide.

2. The heterovesicular liposome of claim 1 further comprising sufficient phosphoric acid encapsulated therein to retard release of the encapsulated compounds.

3. The heterovesicular liposome of claim 1 wherein the liposome is adapted to effect active targeting.

4. The heterovesicular liposome of claim 3 wherein the liposome further comprises a targeting ligand.

5. The heterovesicular liposome of claim 4 wherein the targeting ligand is selected from the group consisting of an antibody, a sugar, a glycolipid, and a protein.

6. A heterovesicular liposome produced by the method comprising:

(a) encapsulating leuprolide in the presence of an organic solvent by forming a first water-in-oil emulsion from two immiscible components;

(b) encapsulating phosphoric acid in the presence of an organic solvent by forming a second water-in-oil emulsion from two immiscible components;

(c) encapsulating the product of step (a) and the product of step (b) by dispersing a chimeric emulsion of the product of step (a) and the product of step (b) in a third immiscible aqueous component to form solvent spherules; and (d) removing organic solvent from the spherules to form the heterovesicular liposome.

7. A method for treating a patient with leuprolide comprising, administering to the patient a heterovesicular liposome comprising at least two different compounds encapsulated in separate chambers of the heterovesicular liposome; wherein one and only one of the compounds is leuprolide.

8. The method of claim 7 wherein a second compound is a biologically active substance other than leuprolide.

* * * * *